(12) United States Patent
Pinault

(10) Patent No.: US 11,452,488 B2
(45) Date of Patent: Sep. 27, 2022

(54) ROBOT AND ROBOT ASSEMBLY FOR PATIENT POSITIONING

(71) Applicant: LEONI KABEL GMBH, Roth (DE)

(72) Inventor: Samuel Pinault, Chevreuse (FR)

(73) Assignee: BIZLINK INDUSTRY GERMANY GMBH, Roth (DE)

( * ) Notice: Subject to any disclaimer, the term of this patent is extended or adjusted under 35 U.S.C. 154(b) by 212 days.

(21) Appl. No.: 16/308,587

(22) PCT Filed: Jun. 26, 2017

(86) PCT No.: PCT/EP2017/065688
§ 371 (c)(1),
(2) Date: May 3, 2019

(87) PCT Pub. No.: WO2018/001951
PCT Pub. Date: Jan. 4, 2018

(65) Prior Publication Data
US 2019/0298276 A1    Oct. 3, 2019

(30) Foreign Application Priority Data
Jun. 27, 2016   (DE) .......................... 102016211538.3

(51) Int. Cl.
*A61B 6/04* (2006.01)
*A61B 6/00* (2006.01)
*B25J 9/16* (2006.01)
*B25J 9/04* (2006.01)
(Continued)

(52) U.S. Cl.
CPC .......... *A61B 6/0487* (2020.08); *A61B 6/4458* (2013.01); *B25J 9/0009* (2013.01);
(Continued)

(58) Field of Classification Search
None
See application file for complete search history.

(56) References Cited

U.S. PATENT DOCUMENTS 5,155,423 A * 10/1992 Karlen ..................... B25J 9/046
                                                              318/568.1
8,740,880 B2    6/2014 Pinault et al.
(Continued)

FOREIGN PATENT DOCUMENTS

CN    103878792 A    6/2014
CN    104587609 A    5/2015
(Continued)

*Primary Examiner* — Hoon K Song
(74) *Attorney, Agent, or Firm* — Tarolli, Sundheim, Covell & Tummino LLP

(57) ABSTRACT

The disclosure relates to a robot, for example for patient positioning, comprising a robot arm with a plurality of robot elements, which are connected to one another by means of shaft units. The shaft units define a respective at least one movement axis of the robot arm. The robot arm comprises a first end region, which permits an arrangement in a surrounding area of the robot, and a second end region, on which an end effector can be arranged. A first shaft unit arranged after the first end region defines a first rotational axis of the robot arm. The robot arm can be arranged in the surrounding area by means of the first end region in such a way that the first rotational axis runs at an angle transverse to the surrounding area.

17 Claims, 7 Drawing Sheets

(51) Int. Cl.
*B25J 9/00* (2006.01)
*A61N 5/10* (2006.01)
*B25J 17/02* (2006.01)
*A61B 6/03* (2006.01)

(52) U.S. Cl.
CPC ............ *B25J 9/046* (2013.01); *B25J 9/1643* (2013.01); *A61B 6/032* (2013.01); *A61B 6/582* (2013.01); *A61N 5/1049* (2013.01); *A61N 2005/1063* (2013.01); *B25J 9/04* (2013.01); *B25J 9/1633* (2013.01); *B25J 17/02* (2013.01)

(56) References Cited

U.S. PATENT DOCUMENTS

| | | | |
|---|---|---|---|
| 2005/0234327 A1* | 10/2005 | Saracen | A61B 6/4458 600/407 |
| 2008/0301872 A1 | 12/2008 | Fahrig et al. | |
| 2010/0237257 A1 | 9/2010 | Saracen et al. | |
| 2015/0027818 A1 | 1/2015 | Bellota | |
| 2019/0110850 A1* | 4/2019 | Hares | A61B 34/30 |

FOREIGN PATENT DOCUMENTS

| | | | |
|---|---|---|---|
| CN | 104873211 A | 9/2015 | |
| CN | 105534676 | 5/2016 | |
| DE | 102007046080 | 4/2009 | |
| DE | 102009035637 | 3/2010 | |
| EP | 1985237 A1 | 10/2008 | |
| EP | 2745997 | 6/2014 | |
| WO | 2006124434 A2 | 11/2006 | |

\* cited by examiner

ROBOT AND ROBOT ASSEMBLY FOR PATIENT POSITIONING

RELATED APPLICATION

This application filed under 35 U.S.C. § 371 is a national phase application of International Application Serial Number PCT/EP2017/065688 filed Jun. 26, 2017, which claims priority to German Patent Application No. 10 2016 211 538.3 filed on Jun. 27, 2016, the disclosure of which is entirely incorporated herein by reference.

TECHNICAL FIELD

The disclosure relates to a robot and a robot assembly as well as a robot worked for patient positioning.

BACKGROUND ART

In an imaging medical examination, such as radiography, computed tomography or nuclear magnetic resonance, for example, and in medical radiotherapy, patients and the relevant medical devices must be positioned relative to one another and/or moved towards one another in a desired manner. For example, in radiotherapy it must be ensured that only diseased tissue is irradiated, but not healthy tissue. For older or disabled patients in particular, a great effort is necessary for precise positioning and a maximum precision/positioning with minimal deviation cannot be achieved, so that a larger area often has to be irradiated due to this and even healthy tissue, for example, is affected by this.

By contrast, existing kinematic systems for patient positioning, for example in the form of a linearly movable patient table, provide only limited movement opportunities of the patient.

A requirement thus exists to provide a system that makes possible improved positioning and/or movement of a patient relative to medical devices.

DISCLOSURE OF THE INVENTION

A robot, for example for patient positioning, is provided for this. The robot comprises a robot arm with a plurality of robot elements, which are connected to one another by means of shaft units. The shaft units define a respective at least one movement axis of the robot arm. The robot arm comprises a first end region, which permits an arrangement in a surrounding area of the robot, and a second end region, on which an end effector can be arranged. A first shaft unit arranged after the first end region defines a first rotational axis of the robot arm. The robot arm can be arranged in the surrounding area by means of the first end region in such a way that the first rotational axis runs at an angle transverse to the surrounding area. Expressed another way, the robot arm can be arrangeable/arranged by means of the first end region in the surrounding area in such a way that the first rotational axis runs at an angle inclined to the surrounding area. The inclination to the surrounding area can be understood as any inclination diverging from 0° and 90°, for example.

In other words, the inventors have developed a robot with a novel kinematic structure, which makes it possible to position patients particularly precisely and with little effort relative to medical devices of the type named at the beginning. As explained below, this kinematic structure is distinguished in particular by a high robustness, compactness and reliability, since, for example, collisions with the surroundings can be better avoided. It likewise permits an arrangement of the end effector especially close to the floor and thus a correspondingly enlarged working area.

The shaft units can be motor-driven articulated units, as known, which define linear and/or rotational axes. These can respectively form movement axes, around or along which the robot elements coupled to the shaft units can move. At least the first rotational axis can be formed generally by a driven rotational link and comprise a motor, for example a servomotor, for this. In a specific embodiment, the robot arm has exclusively rotational axes, and can, as explained below, be arranged additionally as a whole on a linear shaft, which forms the surrounding area.

The robot elements can form rigid sections in a known manner, which are coupled to the corresponding shaft units and form individual kinematic elements of the robot arm. For example, the robot arm can generally have an open kinematic chain, wherein the robot elements form the individual kinematic elements of this chain. Here the kinematic chain can extend from the first end region, which is rigidly coupled to the surrounding area, for example, into the room and by means of its movement axes can position the second end region of the robot arm and the end effector coupled thereto in the room in a desired manner. It can generally be further provided, starting out from the first end region, to number the shaft units and the movement axes determined by these in ascending order. In the case of an open kinematic chain, a next-higher shaft unit can be arranged directly after the preceding shaft unit in each case. For example, the third rotational axis follows the second rotational axis, which is arranged in turn after the first rotational axis, wherein the respective rotational axes are connected to one another by means of individual robot elements.

The robot elements and/or the shaft units can further comprise hollow regions, in order to lead cables, lines or similar in these. This makes it possible that no cables or only a few cables that could enlarge the interference contour of the robot or could get caught in the surroundings have to be led along the outside of the robot arm.

The end effector is, for example, a handling unit and/or in particular a patient table, which can have a table surface for a patient. Here a connection region of the patient table to the second end region of the robot arm can be arranged outside of a central area of the table surface, and in particular outside of a geometrical centre of the table surface. In other words, the robot arm can be coupled to the patient table in an area eccentric to its table surface. Figuratively speaking, the patient table can thus freely overhang the robot arm or project from this. The robot arm can further be coupled to the patient table on an underside of this and generally raise or support the patient table from underneath.

For the arrangement in the surrounding area, the first end region can further comprise in a known manner a coupling region and/or suitable coupling elements, for example bolts can that be inserted into holes in the first end region. The coupling region can likewise facilitate a coupling to a linear shaft unit explained below, in order to be able to move the robot arm additionally in the room. The arrangement can thus include a mechanical coupling to the surroundings and in particular an attachment thereto.

Due to the choice of the aforementioned angle for the first rotational axis, this can generally be arranged inclined or between a horizontal and a vertical spatial plane. The surrounding area can further define a level that is planar, for example, to which the rotational axis is correspondingly inclined. In other words, the robot arm can extend, so to speak, at a slant or obliquely relative to the surrounding area.

Overall a compact design of the robot can be achieved by this and, in particular when used for patient positioning, a particularly suitable mobility as well as a preferred force/torque transfer behaviour. For example, the inventors have recognised that the first rotational axis running at a slant reduces so-called backlash faults and can furthermore handle eccentric or jib-like load transfer areas particularly reliably with a compact configuration. Thus even the drive units of the individual shaft units (for example, in the form of motors such as servomotors) can be formed more compact and less powerful or can move higher loads with the same or a more compact design.

In particular, the inventors have recognised that the present kinematics are advantageous for the supporting and lifting of loads by an introduction of force on the underside (thus figuratively speaking for a supporting or lifting of the loads from underneath). This load case is attended in particular by high pressure and bending forces acting on the robot arm.

It can further be provided in this connection that the first rotational axis runs at an angle of between approx. 10° and approx. 80°, for example at an angle of approx. 20° to approx. 70° and for example approx. 45°, to the surrounding area. It can also be provided that the first rotational axis runs at an angle of approx. 30° to approx. 60° or approx. 40° to approx. 50° to the surrounding area.

According to a further development, it is provided that the first end region comprises a connection plane, which encloses a same angle with the first rotational axis as the surrounding area. For example, the connection plane can extend here parallel to the surrounding area. In other words, it can be provided accordingly that the first shaft unit or at least its first rotational axis is inclined also inside the structure of the robot, in particular related to the connection plane of the first end region. Here the connection plane can comprise or form the coupling area of the first end region described above. In particular, the connection plane can have a plate-shaped component, which can further be connected on its upper side to the first shaft unit and faces the surrounding area with its lower side. The lower and upper side extend here substantially parallel to one another, for example.

It can further be provided that the surrounding area comprises a substantially horizontal spatial plane and, for example, a floor plane. The robot can accordingly be formed generally to fasten the robot arm by means of the first end region on a horizontal plane and in particular on a floor plane. The horizontal spatial plane can likewise be formed by a linear shaft unit explained below, by means of which the robot can be moved in the room.

According to another aspect, the connection plane is coupled by at least two coupling elements to the surrounding area and a connection area of the first shaft unit to a first robot element is arranged substantially between the coupling elements. As already mentioned, the coupling elements can be fastening elements such as bolts and/or elements for coupling to another linear shaft unit, on which the robot is arranged, such as, for example, bearing or guiding elements and/or drive units (for example, linear motors) or units that can be coupled thereto.

By arranging the connection area between the coupling elements, a force transmission into the surrounding area and thus the support of the robot on the surrounding area can be improved.

In particular, the lever arms impairing stability can thus be reduced. The term "between" can refer here to an arrangement in any intermediate space between the two coupling elements. In particular, the connection area and the coupling elements can lie at different height levels/have different height levels. It can also be understood by this that with a projection into a common plane and connection of the coupling elements by means of an imaginary line, the connection area lies at any position along this line and thus between the coupling elements (but not necessarily directly on this line).

It is noted that due to the inclined position of the first rotational axis, lever arms impairing the stability can also therefore be reduced, as the connection point to the first robot element can be arranged at a reduced vertical distance to the surrounding area. This applies in particular by comparison with known robot kinematics with an upright vertical first rotational axis.

In this connection it can further be provided that the connection plane comprises at least four coupling elements, which are arranged in different corner regions of the connection plane and span a substantially rectangular area. Here the connection plane can comprise in particular a plate-shaped component with corresponding corner regions. In this case the connection area of the first shaft unit can be arranged substantially in the area of a diagonal intersection point of the rectangular area. Likewise it can generally be provided that the connection area is arranged substantially centrally between at least two of the coupling elements.

A further development provides that the robot arm further comprises a second shaft unit arranged after the first shaft unit, which second shaft unit defines a second rotational axis of the robot arm. As explained, this can be in particular a shaft unit arranged directly after inside a kinematic chain of the robot arm and the shaft units are coupled to one another by means of a common robot element, for example.

In this connection the robot arm can be formed to position the second shaft unit close to the surrounding area, for example in such a way that it lies directly opposite the surrounding area. A rotation range of the first shaft unit can be selected accordingly to this end and/or a robot element connecting the first and second shaft unit can be designed accordingly. For example, this robot element is, however, substantially straight (and/or cylindrical). It can be provided accordingly that the robot arm can be oriented in such a way via its shaft units that the second shaft unit can be arranged in particular close to a floor area, to which the robot is coupled, and generally close to the first end region of the robot. In this case distances between approx. 2 cm and approx. 50 cm and for example approx. 5 cm and approx. 20 cm or approx. 2 cm and 10 cm to the corresponding surrounding area can generally be provided.

it can further be provided in this connection that the first and second rotational axis of the robot arm are twisted by approx. 90° relative to one another and generally that these are connectable by a straight line, which is substantially perpendicular to both rotational axes. The connecting straight line can extend in this case along a robot element connecting the corresponding shaft units. In other words, the first and second rotational axis (at least in a projection into a common plane) can run substantially perpendicular relative to one another. As a result, the second rotational axis can thus also be inclined to the surrounding area or can be arranged with a corresponding orientation relative to the surrounding area.

Due to the kinematic sequence of a first rotational axis running at a slant and a second rotational axis substantially perpendicular to this, particularly great mobility is achieved in a compact space, in particular when arranging the robot on a horizontal surrounding area and in particular for patient positioning relative to medical devices. As explained below, the robot can accordingly be formed and operable even particularly close to the floor, which reduces the risk of collision with adjacent devices. In the case of a patient table arranged on the robot arm, this also facilitates a simple and convenient access to the patient table, as this can likewise be arranged at a short distance from the floor.

The robot can further comprise a third shaft unit arranged after the first and second shaft unit, which defines a corresponding third rotational axis of the robot arm, and, optionally, also fourth and fifth shaft units arranged after the third shaft unit, which units define corresponding fourth and fifth rotational axes of the robot arm. As in the above case, the respective shaft units can follow one another directly within a kinematic chain and/or be coupled to one another by means of common robot elements. It can be provided as a whole that the robot arm accordingly comprises no more than five rotational axes, wherein these form, for example, the sole movement axes inside the robot arm. The inventors have recognised that this number of robot axes, in particular in interplay with the inclined basic kinematics described above, permits a reliable and adequate mobility for patient positioning, wherein at the same time a compact design of the robot can be retained.

The first and the second shaft unit can be coupled here by means of a turret segment.

The third, fourth and fifth shaft unit can form a generally known robot wrist unit. For example, the rotational axes of these (third to fifth) shaft units are further each oriented orthogonally at least to the immediately preceding rotational axis. All rotational axes of these shaft units can also each run orthogonally to one another or be orientable in such a way, at least during normal operation of the robot (lifting and supporting a patient table from underneath).

In this connection it can further be provided that the third rotational axis runs substantially perpendicular to the second rotational axis.

According to a further aspect, the second and the third shaft unit are spaced between approx. 30 cm and approx. 2 m from one another, and for example between approx. 60 cm and approx. 1.50 m. A distance of approx. 60 cm to approx. 1.20 m can also be provided. According to this variant, the third shaft unit and if applicable other shaft units connected thereto, which together form a wrist unit of the robot arm, for example, can thus be arranged at a certain minimum distance to the first and second shaft unit. The distance can be defined here by a robot element connecting the second and third shaft unit and/or be measured along this.

This results in the first and second shaft unit being able to he arranged at a distance from the second end region of the robot arm, which can be advantageous with regard to avoiding a collision. For example, it can be facilitated by this that the second end region of the robot can be arranged at a distance from the comparatively large first and second (basic) shaft units and thus a comparatively large amount of free space is available in its vicinity. In other words, the robot can have a comparatively small size and thus reduced interference contour close to the second end region. This end region can consequently be positioned even in comparatively tight working areas, for example close to or inside medical devices.

The disclosure further relates to a robot assembly, comprising a robot according to one of the previous aspects, wherein the surrounding area comprises a linear shaft unit (and/or is formed by this), on which the robot arm can be arranged by means of its first end region. The overall working space of the robot can be increased by this and in particular assume a generally cylindrical shape.

The linear shaft unit can be coupled in a known manner to the robot, and move this linearly in the room. As already indicated, this can take place by means of a connection plane and/or a coupling area of the first end region of the robot arm. Furthermore, coupling elements can be used for this, such as, for example, guide or bearing elements or also drive units e.g. in the form of linear motors or units that can be coupled thereto, so that the robot can be moved along a guide rail of the linear shaft unit, for example.

In this connection the linear shaft unit can define a linear movement axis, which encloses a same angle with the first rotational axis of the robot as the surrounding area. In other words, the linear movement axis, along which the robot is movable, can extend parallel to a horizontal surrounding area, for example, and/or to a connection plane of the first end region of the robot arm. Generally the first rotational axis of the robot arm can thus likewise run at a slant is to the linear movement axis. It is noted that the linear movement axis can facilitate a translation of the robot in a known manner within a plane, but in this case can also define a curved or bent movement path.

It can be provided that the linear shaft unit can be arranged on a floor area. In this case also it can thus be guaranteed that the robot can operate especially close to the floor and thus has a reduced interference contour and a preferred mobility due to the first rotational axis running at a slant.

According to another aspect, a known calibration of the kinematic and/or elastic properties of the robot (and in particular of its robot arm) can be carried out at several positions of the linear axis and, for example, at uniform intervals along the linear axis. Corresponding calibration data can thus be obtained by way of interpolations or similar for each position along the linear axis and can be stored, which data can be referred to during control of the robot. A high positioning accuracy along the entire linear axis can thus be guaranteed, as local interactions between the robot and the linear axis can be taken into account.

The linear shaft unit can further be modular in construction, for example in the form of individual modules of approx. 1 in in length, in order to adapt the extension of the linear axis flexibly.

Finally, the disclosure also relates to a robot workcell, comprising a floor area and a robot assembly according to one of the previous aspects, wherein the linear shaft unit is arranged on the floor area. It can further be provided in this connection that the robot workcell also comprises an imaging medical device and/or a device for medical radiotherapy, wherein the robot assembly is formed to position a patient in a working area of the medical device.

It can be provided for this to arrange the robot assembly and in particular its linear shaft unit inside the robot workcell and relative to any medical devices in such a way that the working areas of the robot assembly and the medical device overlap in a desired manner. In particular, it can be provided in this case that the robot assembly is coupled to a patient table in the manner described above and is formed to position the patient table in a desired manner relative to the devices.

One example provides that an imaging medical device is arranged in such a way relative to the linear shaft unit that a patient oriented by means of the robot can be slid into the working area of the medical device by driving of the linear shaft. This applies for example to known computed tomography scanners, into which the patient must be slid at least partially. The medical device can be arranged at or adjacent to an (axial) end region of the linear shaft for this.

According to another variant, it can be provided that the robot workcell comprises several such medical devices and the robot assembly is formed to position the patient in a desired manner relative to all medical devices in particular by means of a suitable extension of the linear shaft unit. This permits increased flexibility inside a treatment room, as a patient can be moved with little effort and maintaining a desired positioning between an imaging device (for example, a computed tomography scanner) and a device for radiotherapy. The devices can be arranged for this generally on a common side or opposite sides along the linear shaft and/or across a corner (one device at an axial end of the linear shaft and one laterally along the linear shaft). An opposing arrangement of such devices on or close to corresponding end regions of the linear shaft unit is also conceivable.

BRIEF DESCRIPTION OF THE DRAWINGS

The present disclosure is to be explained further with reference to figures. These figures show schematically:

FIG. 3b a detailed view of a wrist unit of the robot in FIGS. 1 to 3a;

DETAILED DESCRIPTION

In the following, without being restricted to these, specific details are explained to supply a complete understanding of the present disclosure. However, it is clear to a person skilled in the art that the present disclosure can be used in other exemplary embodiments that can deviate from the details explained below.

Figure 1:
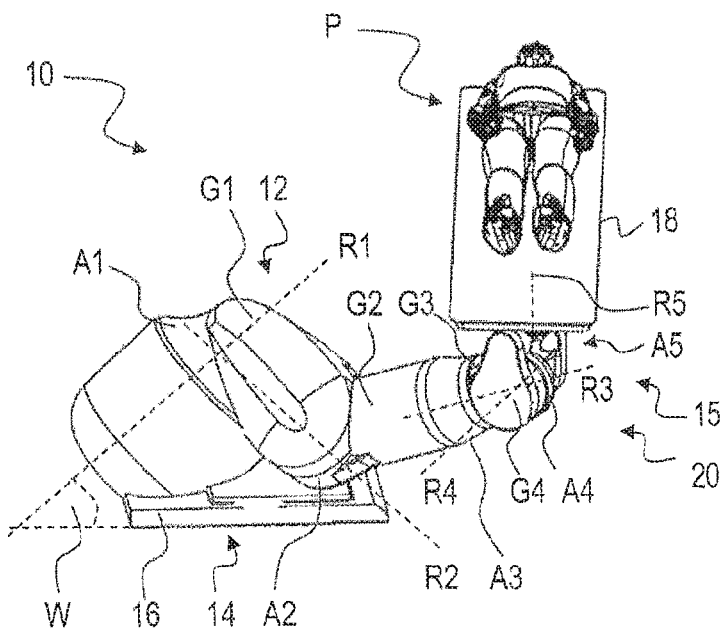
FIGS. 1 to 3 representations in perspective of a robot for patient positioning according to an exemplary embodiment.

FIG. 1 shows a robot 10 according to a first exemplary embodiment. The robot comprises a robot arm 12, which comprises a first end region 14, with which the robot 10 can be arranged on a surrounding area, which is not shown separately, and can be coupled mechanically to this. Here the first end region 14 comprises a plate-shaped component 16, which in the manner described below forms a connection plane and a coupling area to a horizontal spatial plane.

Starting out from the plate-shaped component 16, the robot arm 12 extends in the sense of an open kinematic chain into the room, wherein this chain has a second end region 15 with an end effector in the form of a patient table 18. This is coupled in a known manner to the second end region of the robot arm 12.

In the following the kinematic structure of the robot arm 12 is explained. Starting out from the plate-shaped component 16, the robot arm 12 comprises first a first rotational shaft unit A1, which defines a first rotational axis R1 of the robot arm 12. The first rotational shaft unit A1, like also the other rotational shaft units A2-A5 explained below, here comprises a rotation joint according to a generally known construction that is driven by motor, for example by servomotor. A first robot element G1, which is formed from metal, for example, and thus generally rigidly formed, extends starting out from the first shaft unit A1.

The first robot element G1 extends to a second rotational shaft unit A2, which defines a second rotational axis R2. It is further recognised that although the second rotational axis R2 and the first rotational axis R1 are spaced apart from one another by the robot element G1, they extend perpendicular relative to one another. In other words, these rotational axes R1, R2 enclose a right angle with one another, at least in a state projected onto one another. In the same sense these axes can be connected by a virtual straight line (not shown), which is perpendicular to both rotational axes R1, R2.

Starting out from the second rotational shaft unit A2, a second robot element G2 extends to a third rotational shaft unit A3, which in turn defines a third rotational axis R3. This extends orthogonally to the second rotational axis R2. The connection of the second and third rotational shaft units A2, A3 is accomplished here via a turret segment.

The third rotational shaft unit A3 is part of a wrist unit 20 of the robot arm 12, which comprises in a known manner two other (fourth and fifth) rotational shaft units A4, A5 with associated rotational axes R4, R5, which are connected to one another by means of third and fourth robot elements G3 and G4 (partially concealed in FIG. 1). The rotational axes R3-R5 of the wrist unit 20 are also perpendicular in a known manner to the previous one in each case and in normal operation (e.g. raising and supporting the patient table 18 from underneath) are arranged so that they are oriented substantially perpendicular to all other axes of the wrist unit 20.

Figure 2:
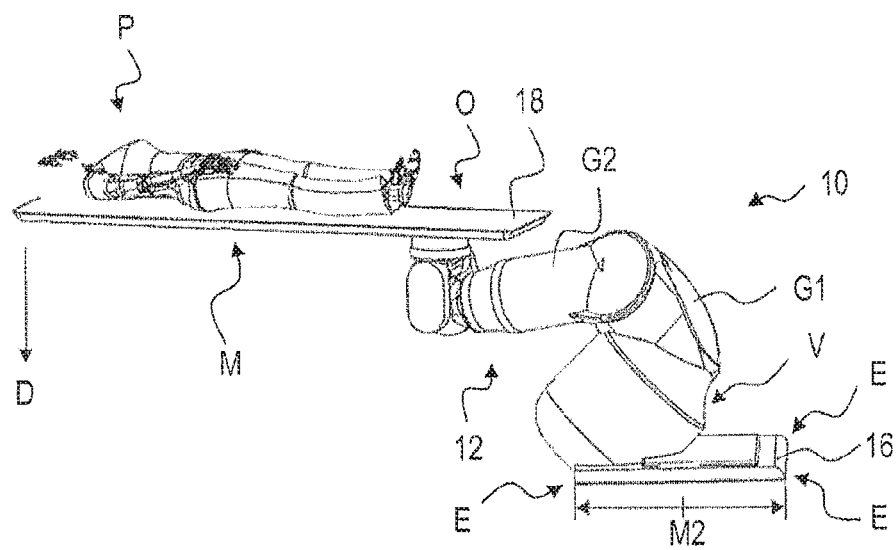

It is recognised in FIG. 2 as a special feature of the present kinematics that the first rotational axis R1 extends at a slant relative to the plate-shaped component 16 and the connection plane to the surroundings defined by this. Put more accurately, the rotational axis R1 runs, for example, at an angle W of 45° to the plate-shaped component 16.

Figure 3:
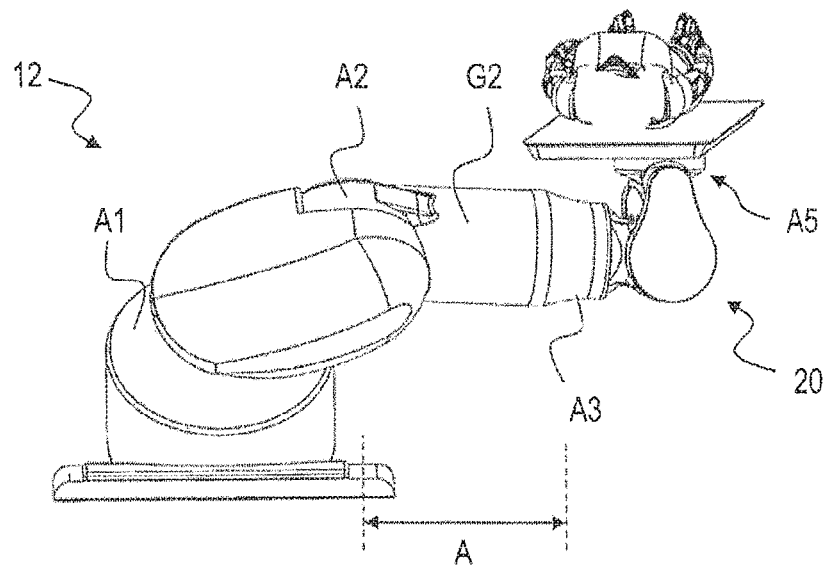

In FIGS. 2 and 3 the robot 10 from FIG. 1 is shown by means of other views in perspective, wherein the robot arm 12 assumes different operating positions in each case.

In FIG. 2 in particular it is recognised that the robot arm 12 is coupled to the patient table 18 with its second connection region 15 close to an edge area and thus eccentric from a geometrical centre M. Here the robot 10 lifts the patient table 18 from underneath and supports this from underneath, so that its upper side O can be used fully as a table surface for a patient P. A load transmission takes place accordingly into the robot arm 12 likewise significantly in an eccentric manner, as indicated by the pressure loading D in FIG. 2. On the other hand, a greater free space results around the patient P, which permits a collision-free arrangement of the patient table 18 close to or inside medical devices.

It is further recognised in FIG. 3 that the second robot element G2 determines a distance A between the second and third rotational shaft units A2, A5, which distance corresponds to 1 m in the present example. Consequently the wrist unit 20 of the robot arm 12 is also arranged at a corresponding distance A to the previous rotational shaft units A1, A2.

This enables the wrist unit 20 to be arranged spaced apart from the rotational shaft units A1, A2 acting as basic shafts, which are also comparatively large, due to which an interference contour close to the wrist unit 20 is reduced. This also contributes to the avoidance of collisions with the surroundings.

Returning to FIG. 2, it is evident that a connection area V of the first rotational shaft unit A1 to the first robot element G1 is arranged above or in the region of the connection plane. Put more accurately, the connection area V is located approximately above a geometrical centre M2 of the plate-shaped component 16. The latter is formed substantially rectangular and comprises in each of its corner regions E coupling elements, which are explained below, for mechanical connection to a linear shaft unit L (not all corner regions E are to be recognised here in FIG. 2). The connection area V thus lies substantially above a diagonal intersection point of the corner regions E and between all and in particular respectively two opposing coupling elements. This reduces the effective lever arms and makes possible reliable support and force transmission into the plate-shaped component 16 and the surrounding area coupled to it.

Figure 3A:
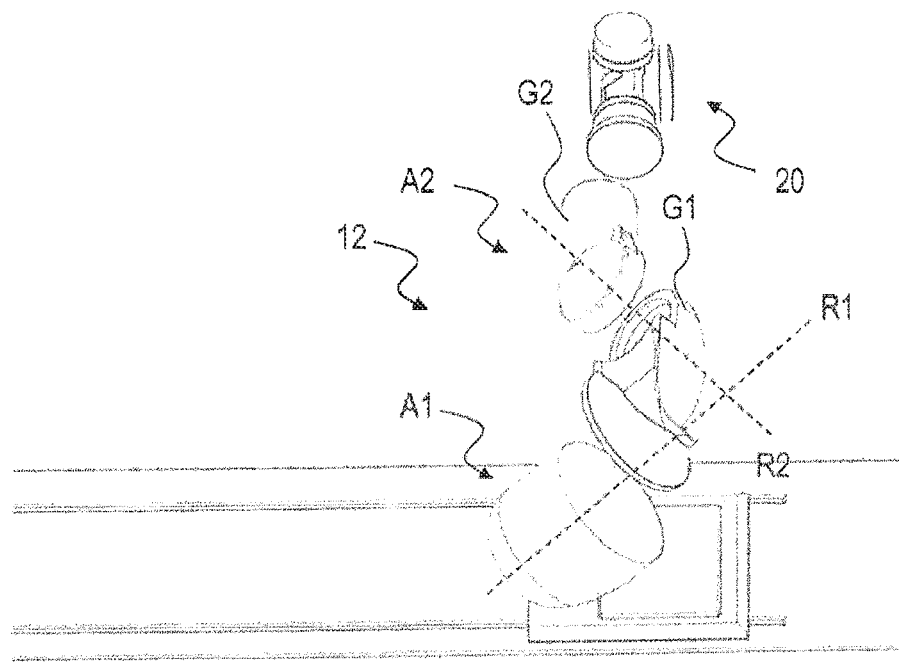
FIG. 3a an exploded representation of the robot arm of the robot according to FIGS. 1 to 3

In FIG. 3a the robot arm 12 of the robot 10 is shown in an exploded representation. The position of the individual shaft units A1-A5 is recognised again here as well as the extension of the robot elements G1-G4. It is discernible in particular that the robot element G1 connecting the first and second shaft unit is constructed in the form of a turret segment and the rotational axes R1 and R2 are twisted by 90° relative to one another.

Figure 3B:
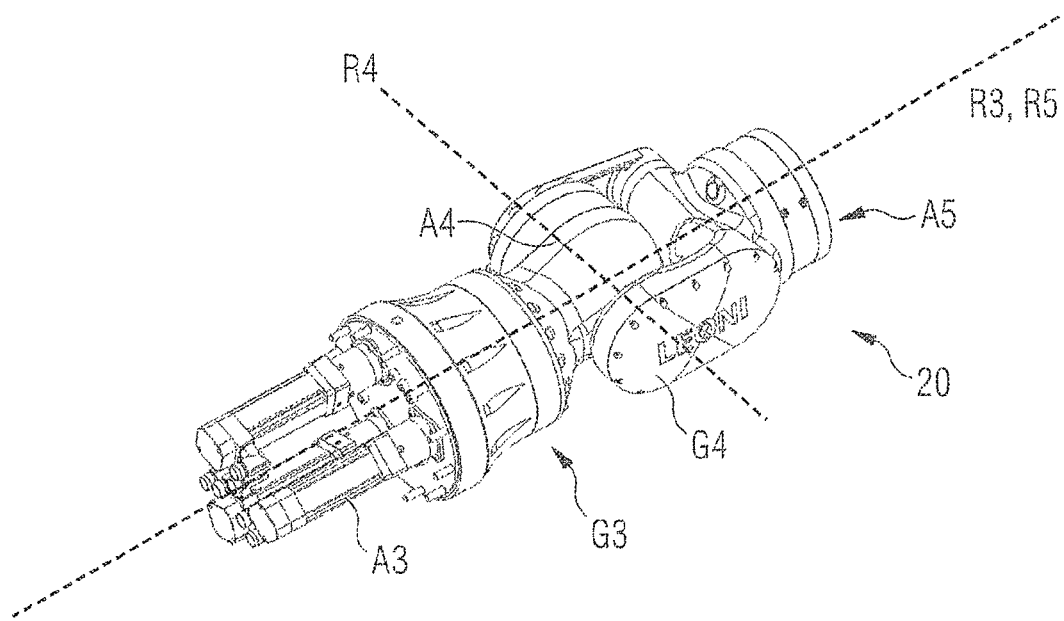

Finally, in FIG. 3b a detailed representation of the wrist unit 20 is shown, which comprises three shaft units A3-A5 in a known manner. In the position shown, the third and fifth rotational axes R3-R5 coincide and are each perpendicular to the fourth rotational axis R4. As shown in FIG. 1, in normal operation (lifting and supporting of the patient table 18 from underneath) the rotational axes R3-R5 are, however, arranged in such a way that all rotational axes R3-R5 run substantially perpendicular relative to one another.

Figure 4:
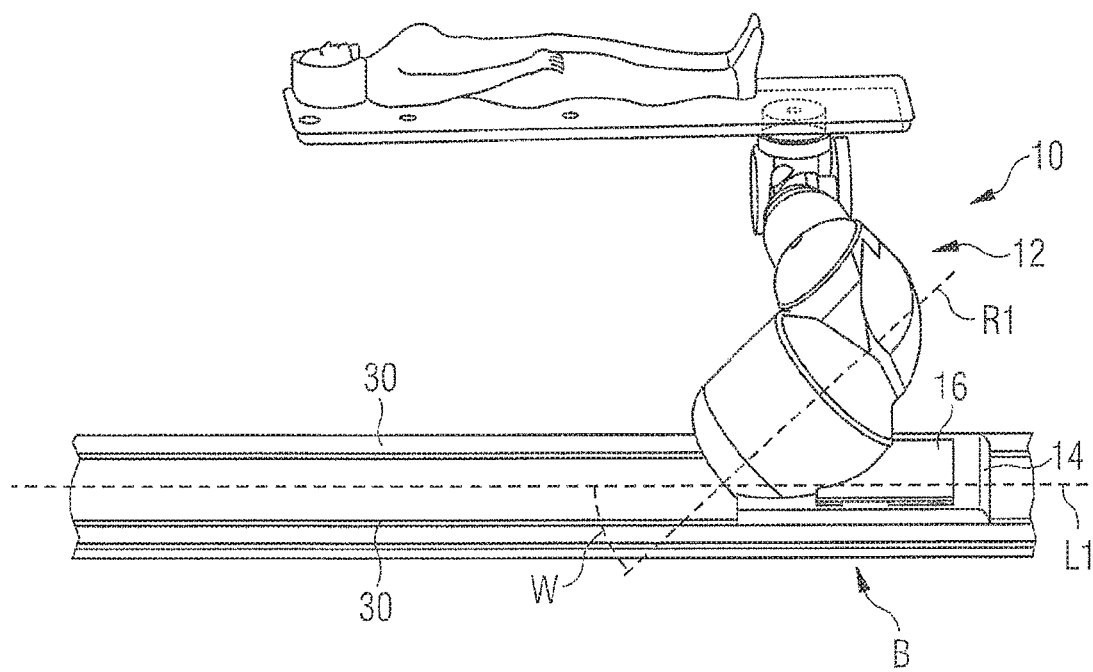
FIG. 4 a representation in perspective of a robot assembly, comprising a robot according to the exemplary embodiment of FIGS. 1 to 3 and a linear shaft unit.

FIG. 4 shows a robot assembly, comprising a robot 10, as explained above with reference to FIGS. 1-3, and a linear shaft unit L. The linear shaft unit L comprises two guide rails 30 parallel to one another and is arranged as a whole on a horizontal level floor surface B in the room. The linear shaft unit L accordingly forms a surrounding area in the form of a horizontal spatial plane, on which robot 10 is arranged. Furthermore, it defines a linear (or translatory) movement axis L1, which likewise extends parallel to the level floor surface B and along which the robot 10 can be moved in the room. To this end the robot arm 12 is connected via the plate-shaped component 16 and, as explained above, the coupling elements arranged thereon, to drive units of the linear shaft unit L, which facilitate a movement along the linear axis L1. The drive units can be formed for example as linear motors and the coupling elements can comprise screw bolts, adhesive points or other attachment elements, in order to couple the robot 10 thereto.

In FIG. 4 the inclination of the first rotational axis R1 of the robot arm 12 is shown again in the form of the angle W to the plate-shaped component 16 or to the connection plane of the first end region 14. It is recognised that the rotational axis R1 encloses the same angle W with the linear shaft unit L and the linear axis L1 and thus also with the level floor surface B parallel to this.

Figure 5A:
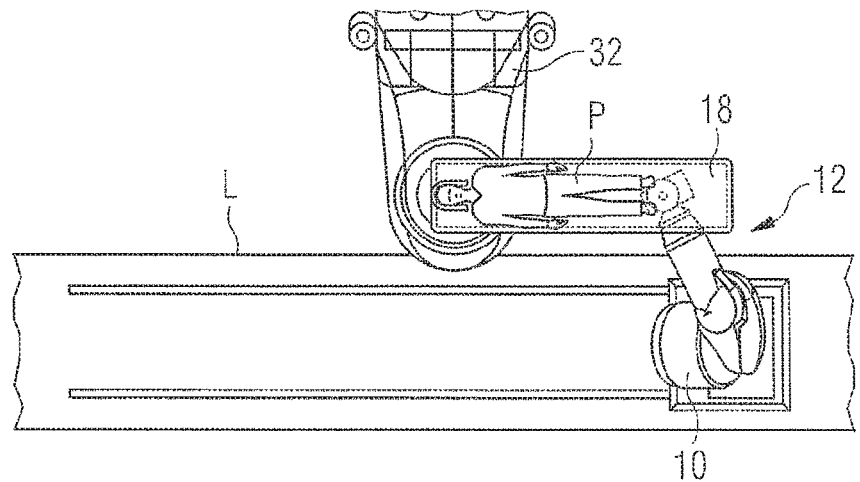
FIG. 5a to c plan views of different operating states of a robot workcell comprising a robot assembly according to FIG. 4.
Figure 5B:
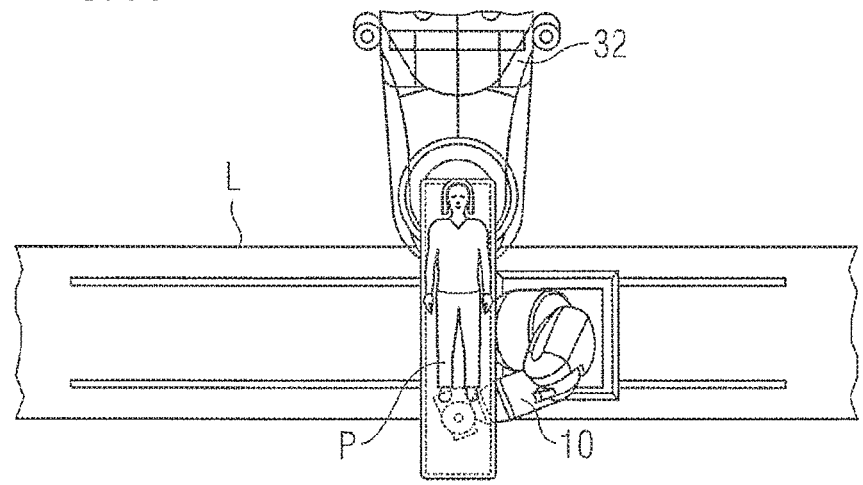
Figure 5C:
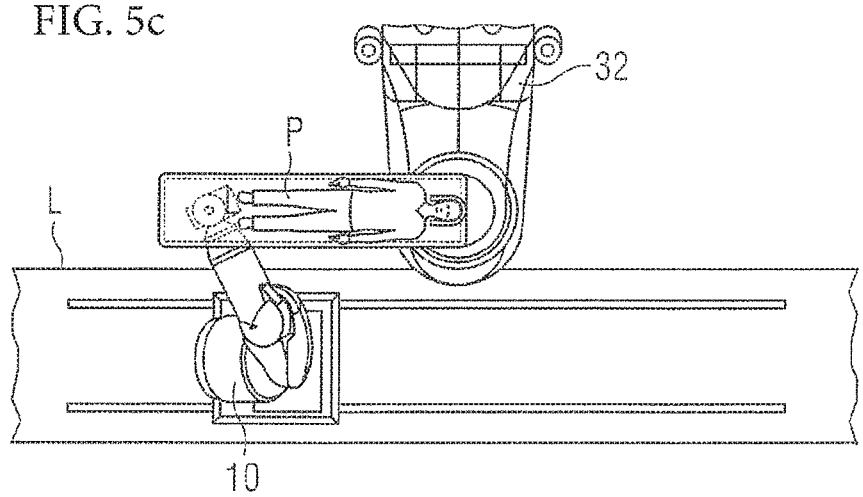

FIGS. 5a-c show plan views of different operating states of a robot workcell, which comprises a robot assembly according to FIG. 4 and a medical radiotherapy device 32. The robot 10 is specifically recognised again with the patient table 18 mounted on it and the linear shaft unit L for moving the robot 10 in the room. FIGS. 5a-c show here by way of example different positions of the individual axes R1-R5 and of the robot elements G1-G4 of the robot arm 12, by means of which a patient P (and in the case shown the patient's head area) can be positioned in an irradiation working area of the medical device 32. Even a continuous movement can take place between the positions shown in FIGS. 5a-c by coordinated activation of the individual robot shaft units A1-A5 and the linear shaft unit L. It is illustrated in particular in FIG. 5b that due to its compact design, the robot 10 has a small interference contour with sufficient rigidity and can thus be moved collision-free close to and along the medical device 32.

Figure 6A:
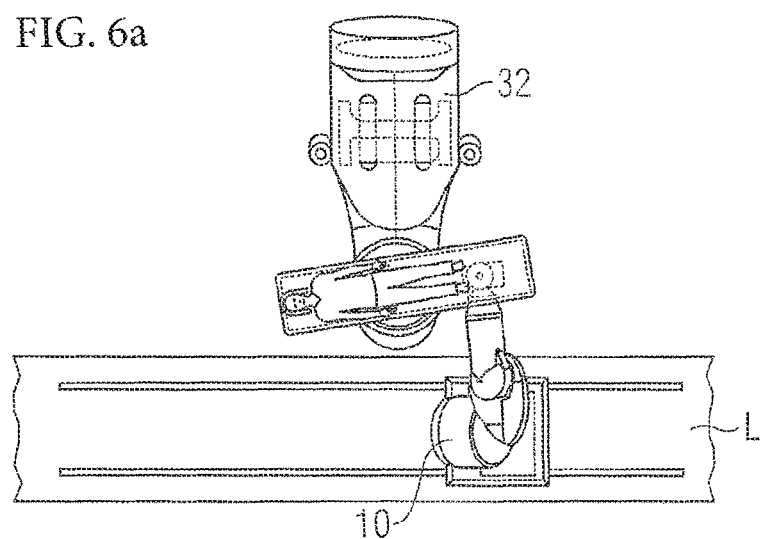
FIG. 6a to c representations in perspective of a robot workcell analogous to FIGS. 5a to c.
Figure 6B:
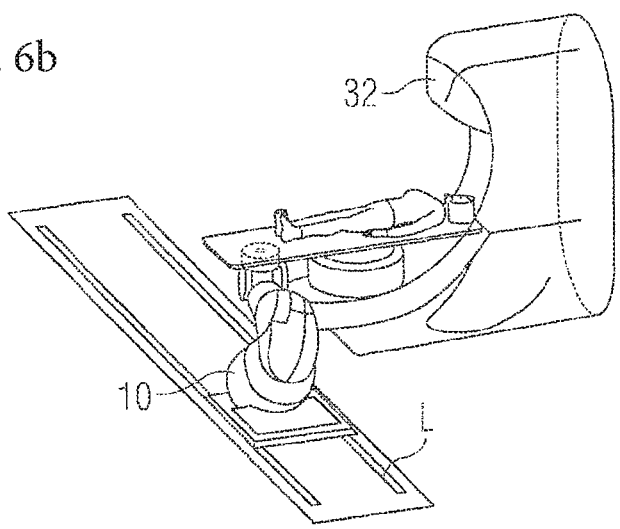
Figure 6C:
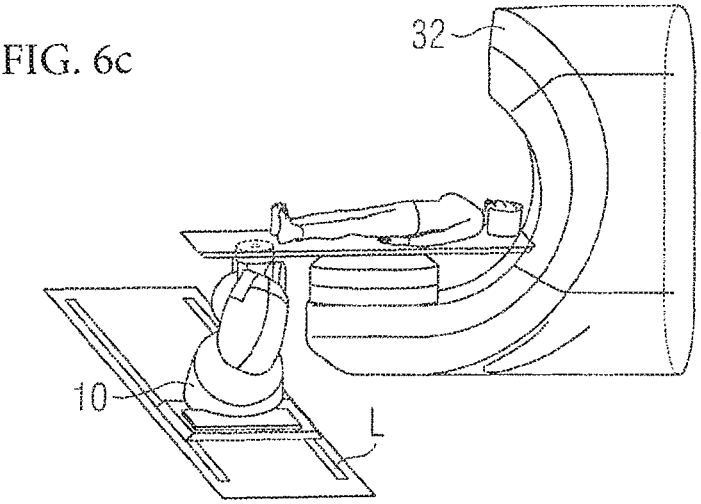

FIGS. 6a-c show by analogy with FIGS. 5a-c other representations in perspective of the robot workcell in different operating states, in which a patient P is positioned and moved by means of the robot 10 in a desired manner relative to the radiotherapy device 32.

Figure 7A:
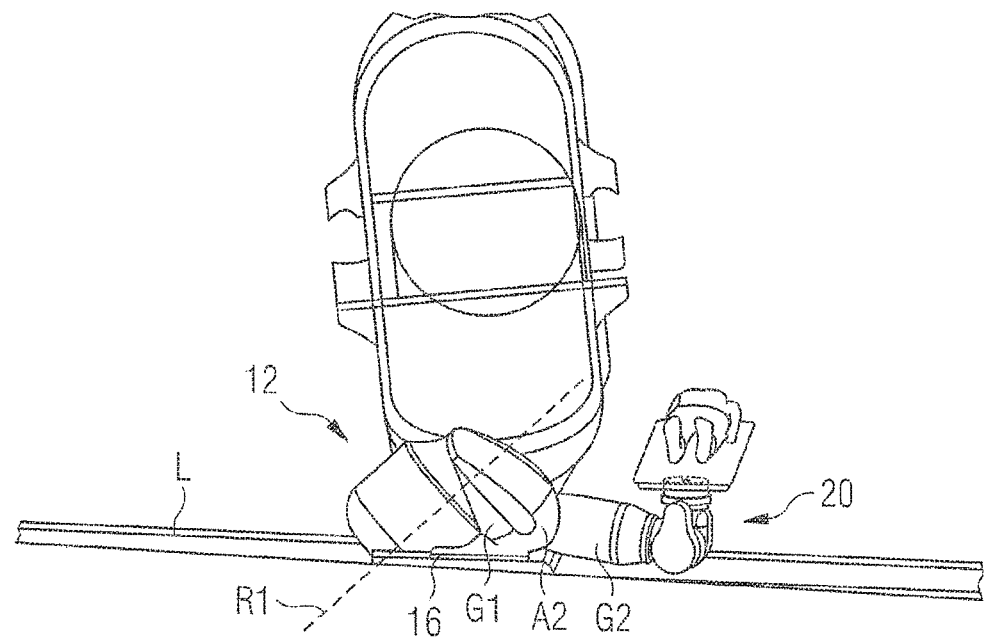
FIG. 7a to b representations in perspective of the robot workcell according to the previous figures, wherein the robot assumes a position especially close to the floor.
Figure 7B:
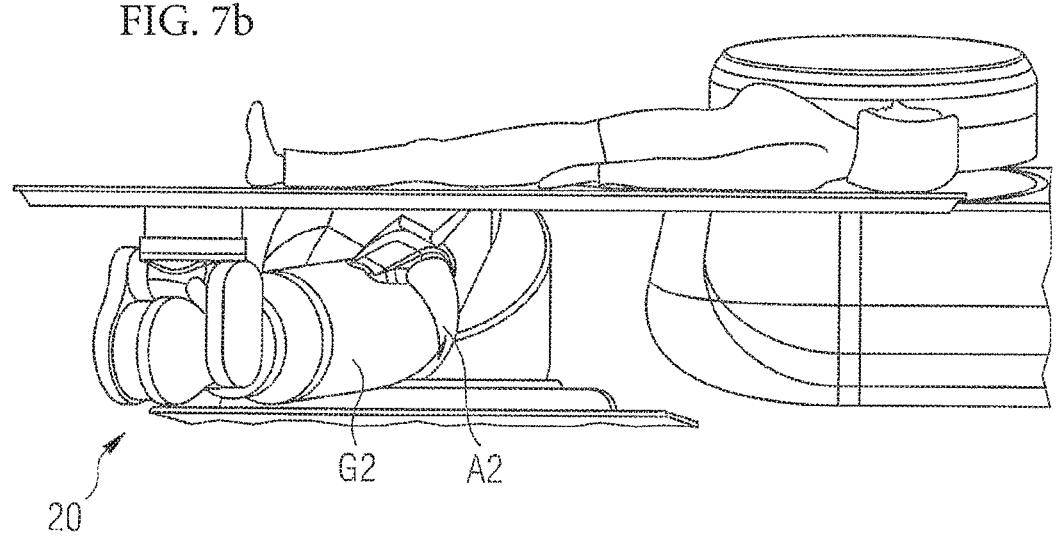

FIGS. 7a-b show representations in perspective of the robot workcell according to the previous figures, wherein the robot 10 assumes a position particularly close to the floor. Put more precisely, it is recognised that the first robot element G1 was rotated by the first rotational axis R1 in the direction of the linear shaft unit L, so that the second rotational shaft unit A2 is arranged directly above the plate-shaped component 16. Starting out from here, the second robot element G2 extends substantially linearly, so that the wrist unit 20 of the robot arm 12 is arranged at a low height (or at a small vertical distance) to a floor area.

Figure 8A:
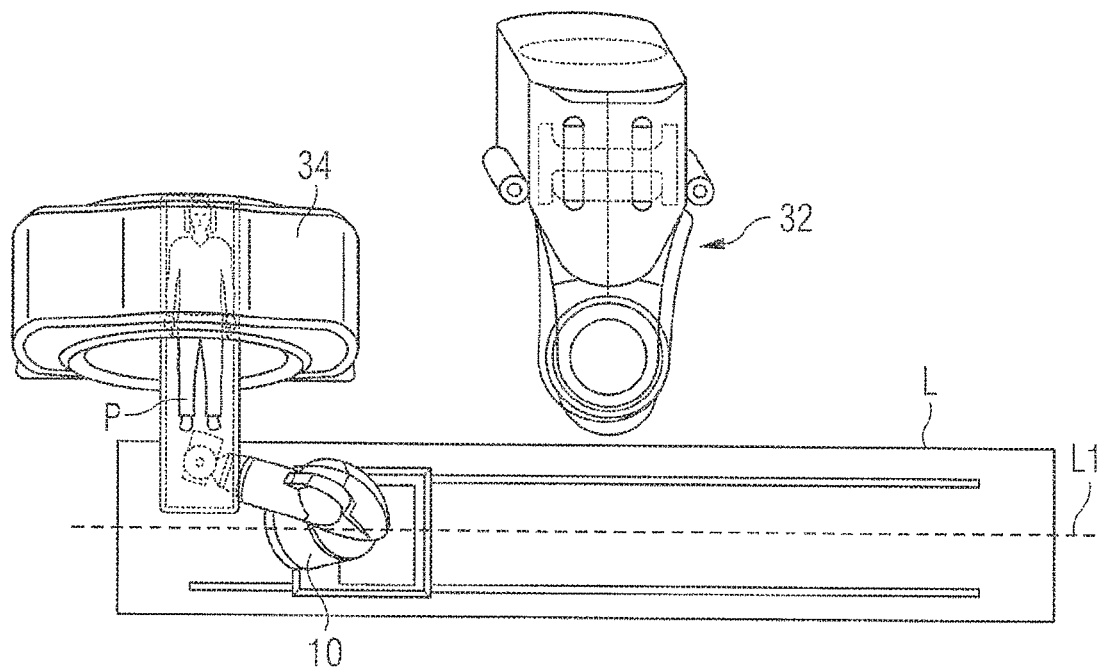
FIG. 8a to b plan views of a robot workcell analogous to the previous figures, comprising a plurality of medical devices.
Figure 8B:
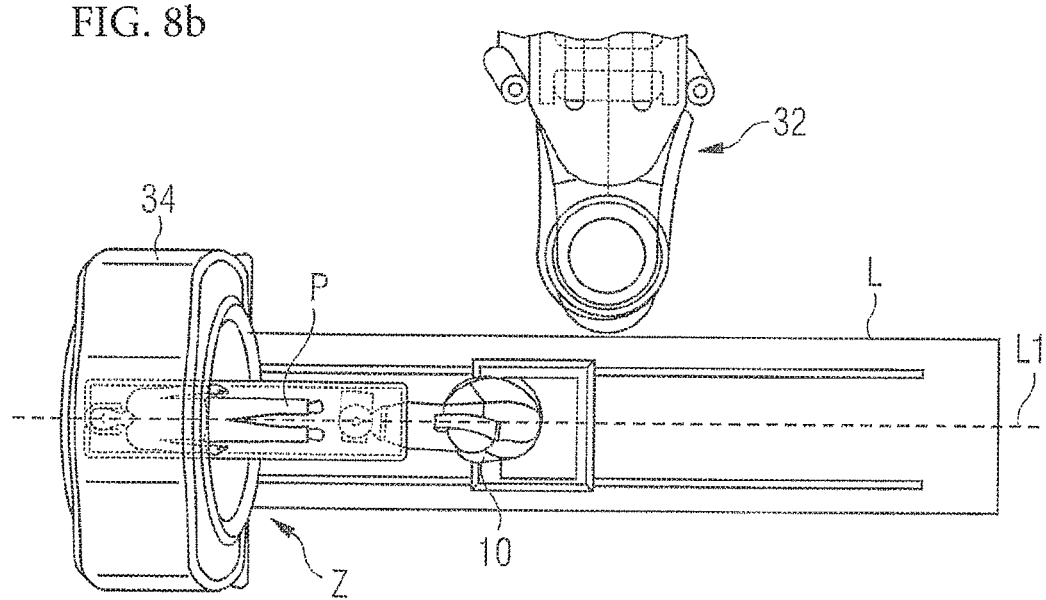

FIGS. 8a-b show finally plan views of a robot workcell analogous to the previous figures, comprising a plurality of medical devices 32, 34. The robot workcells specifically each comprise a radiotherapy device 32 and an imaging computed tomography scanner 34. In the case shown in FIG. 8a, both medical devices 32, 34 are arranged on a common side along the linear axis L1. The linear shaft unit L is arranged here so that the robot 10 can position a patient optionally in the working area of one of the devices 32, 34.

In the case of FIG. 8b, the computed tomography scanner 34 is at one axial end Z of the linear shaft unit L, so that the patient P, following appropriate orientation via the robot 10 (in particular parallel to the linear axis L1) can be slid by means of the linear shaft unit L into the computed tomography scanner 34. At the same time, however, arrangement of the patient P in the working area of the radiotherapy device 32 is still possible. To this end the patient P can be oriented by means of the robot assembly by analogy with the operating positions shown in figure group 5 and 6.

Although the invention has been described with a certain degree of particularity, those skilled in the art can make various changes to it without departing from the spirit or scope of the invention as hereinafter claimed.

The invention claimed is:

1. Robot, for example for patient positioning, comprising a robot arm with a plurality of robot elements, which are connected to one another by means of shaft units,
   wherein the shaft units each define at least one movement axis of the robot arm,
   wherein the robot arm comprises a first end region, which permits arrangement on a surrounding area of the robot via a plate-shaped component defining a substantially horizontal plane, wherein the first end region is directly coupled to the plate-shaped component, wherein the first end region further comprises a connection plane defining a plane of the direct coupling between the first end region and the plate-shaped component, and a second end region, on which an end effector can be arranged, wherein a first shaft unit arranged after the first end region defines a first rotational axis of the robot arm, and wherein the robot arm is be arranged by the first end region in such a way on the surrounding area that the first rotational axis runs at a non-orthogonal angle with respect to the surrounding area, with respect to the plate-shaped component and with respect to the connection plane of the first end region, wherein the surrounding area comprises a substantially horizontal spatial plane and the robot is adapted to fasten the robot arm via the first end region on the horizontal spatial plane such that the angle of the first rotational axis is between approx. 40° and approx. 50° with respect to the surrounding area.

2. Robot according to claim 1, wherein the connection plane substantially encloses a same angle with the first rotational axis as the surrounding area.

3. Robot according to claim 1,
wherein the surrounding area comprises a substantially horizontal spatial plane and for example a floor plane.

4. Robot according to claim 1,
wherein the connection plane is coupled to the surrounding area by at least two coupling elements and a connection area of the first shaft unit to a first robot element is arranged substantially between the coupling elements.

5. Robot according to claim 1,
wherein the robot arm further comprises a second shaft unit arranged after the first shaft unit and which defines a second rotational axis of the robot arm.

6. Robot according to claim 5,
wherein the robot arm is formed to position the second shaft unit close to the surrounding area.

7. Robot according to claim 5,
wherein the robot arm comprises a third shaft unit arranged after the first and second shaft unit, which third shaft unit defines a third rotational axis of the robot arm, and, optionally, also fourth and fifth shaft units arranged after the third shaft unit, which units define corresponding fourth and fifth rotational axes of the robot arm.

8. Robot according to claim 7,
wherein the third rotational axis runs substantially perpendicular to the second rotational axis.

9. Robot according to claim 7,
wherein the second and third shaft unit are spaced between approx. 30 cm and approx. 2 m from one another, and for example between approx. 60 cm and approx. 1.50 m.

10. Robot assembly,
comprising a robot according to claim 1, wherein the surrounding area comprises a linear shaft unit, on which the robot arm can be attached by its first end region.

11. Robot assembly according to claim 10,
wherein the linear shaft unit defines a linear movement axis located in a substantially horizontal plane, which encloses a same angle with the first rotational axis of the robot as the surrounding area.

12. Robot assembly according to claim 10,
wherein the linear shaft unit can be arranged on a floor area.

13. Robot workcell,
comprising a floor area and a robot assembly according to claim 10, wherein the linear shaft unit is arranged on the floor area.

14. Robot workcell according to claim 13,
further comprising an imaging medical examination device and/or a device for medical radiotherapy, wherein the robot assembly is formed to position a patient in a working area of the medical device.

15. Robot according to claim 1,
wherein the first rotational axis runs at an angle of substantially 45°, to the surrounding area.

16. Robot according to claim 1 wherein said plate-shaped component is mounted for translatory horizontal movement with respect to said surrounding area.

17. Robot, for example for patient positioning, comprising a robot arm with a plurality of robot elements, which are connected to one another by means of shaft units, wherein the shaft units each define at least one movement axis of the robot arm, wherein the robot arm comprises a first end region, which permits arrangement on a surrounding area of the robot via a plate-shaped component defining a substantially horizontal plane, wherein the first end region is directly coupled to the plate-shaped component, wherein the first end region further comprises a connection plane defining a plane of the direct coupling between the first end region and the plate-shaped component, and a second end region, on which an end effector can be arranged, wherein a first shaft unit arranged after the first end region defines a first rotational axis of the robot arm, wherein the robot arm is be arranged by the first end region in such a way on the surrounding area that the first rotational axis runs at a non-orthogonal angle with respect to the surrounding area, with respect to the plate-shaped component and with respect to the connection plane of the first end region, wherein the surrounding area comprises a substantially horizontal spatial plane and the robot is adapted to fasten the robot arm via the first end region on the horizontal spatial plane such that the angle of the first rotational axis is between approx. 40° and approx. 50° with respect to the surrounding area, wherein the connection plane substantially encloses a same angle with the first rotational axis as the surrounding area, wherein said robot arm further comprises a second shaft unit arranged after the first shaft unit and which defines a second rotational axis of the robot arm, and wherein the robot arm comprises a third shaft unit arranged after the first and second shaft unit, which third shaft unit defines a third rotational axis of the robot arm, and, optionally, also fourth and fifth shaft units arranged after the third shaft unit, which units define corresponding fourth and fifth rotational axes of the robot arm.

* * * * *